US005239987A

United States Patent [19]

Kaiser et al.

[11] Patent Number: 5,239,987

[45] Date of Patent: Aug. 31, 1993

[54] ANATOMICALLY CORRECT CONTINUOUS PASSIVE MOTION DEVICE FOR A LIMB

[75] Inventors: Robert T. Kaiser, Mount Laurel, N.J.; George Telepko, Fort Washington, Pa.; Vero Ricci, Collingswood, N.J.; Robert J. Drozdowski, Langhorne, Pa.; Berdj C. Kalustyan, Moorestown, N.J.

[73] Assignee: Jace Systems, Moorestown, N.J.

[21] Appl. No.: 802,911

[22] Filed: Dec. 6, 1991

[51] Int. Cl.[5] .................... A61F 5/00

[52] U.S. Cl. .................... 128/25 R; 128/25 B

[58] Field of Search .................... 128/25 R, 25 B, 25 C, 128/26

[56] References Cited

U.S. PATENT DOCUMENTS

| | | | |
|---|---|---|---|
| D. 296,364 | 6/1988 | Nippoldt et al. . | |
| D. 298,569 | 11/1988 | Nippoldt et al. . | |
| D. 298,570 | 11/1988 | Nippoldt et al. . | |
| 3,760,801 | 9/1973 | Borgeas | 128/25 R |
| 4,323,060 | 4/1982 | Pecheux . | |
| 4,402,502 | 9/1983 | Peters . | |
| 4,474,176 | 10/1984 | Farris et al. | 128/25 B |
| 4,492,222 | 1/1985 | Hajianpour | 128/25 R |
| 4,509,509 | 4/1985 | Bouvet et al. . | |
| 4,520,827 | 6/1985 | Wright et al. . | |
| 4,546,763 | 10/1985 | Coutts | 128/25 R |
| 4,549,534 | 10/1985 | Zagorski et al. | 128/25 R |
| 4,558,692 | 12/1985 | Greiner | 128/25 R |
| 4,566,440 | 1/1986 | Bermer et al. | 128/25 R |
| 4,587,960 | 5/1986 | Schotten | 128/25 R |
| 4,601,468 | 7/1986 | Bond et al. . | |
| 4,602,618 | 7/1986 | Berze | 128/25 R |
| 4,603,687 | 8/1986 | Greenwood | 128/25 R |
| 4,621,620 | 11/1986 | Anderson | 128/25 R |
| 4,637,379 | 1/1987 | Saringer | 128/25 R |
| 4,665,899 | 5/1987 | Farris et al. | 128/25 R |
| 4,671,257 | 6/1987 | Kaiser et al. | 128/25 R |
| 4,751,917 | 6/1988 | Ruf | 128/25 R |
| 4,807,601 | 2/1989 | Wright | 128/25 R |
| 4,825,852 | 5/1989 | Genovese et al. | 128/25 R |
| 4,834,073 | 5/1989 | Bledsoe et al. | 128/25 R |
| 4,930,497 | 6/1990 | Saringer | 128/25 R |

*Primary Examiner*—Richard J. Apley
*Assistant Examiner*—Linda C. M. Dvorak
*Attorney, Agent, or Firm*—Panitch Schwarze Jacobs & Nadel

[57] ABSTRACT

A bilateral anatomically correct continuous passive motion orthosis device for a limb having pivotally connected first and second body portions. The device includes a base having a proximal end and a distal end. A first carriage member receives the first body portion and is pivotally connected to a second carriage member which receives the second body portion. The second carriage member is also pivotably connected to the base. A drive mechanism moves the first carriage member between the distal and proximal ends of the base. A speed control device controls the velocity of the first carriage member between the distal and proximal ends of the base such that the first carriage member pivots about a first support pivot axis with respect to the second carriage member at a predetermined angular velocity. A biasing mechanism is provided to assist the drive mechanism in lifting the limb. The second carriage member is pivotally connected to the base such that its virtual pivot axis is spaced from the base to permit bilateral use of the device.

6 Claims, 9 Drawing Sheets

ANATOMICALLY CORRECT CONTINUOUS PASSIVE MOTION DEVICE FOR A LIMB

FIELD OF THE INVENTION

The present invention relates to exercise devices and, more particularly, to a device which anatomically receives a joint of a human patient and passively and continuously exercises the same.

BACKGROUND OF THE INVENTION

In the past, postoperative and post-trauma treatment of patients's joints commonly included immobilization. The affected joints were fixed by casts or traction for an extended duration. As a result of such immobilization various medical problems commonly arose. In particular, capsular, ligamentous and articular adhesions, thromboembolism, venos stasis, post-traumatic osteopenia, peripheral edema, muscle atrophy, and the like were commonly attributed to the immobilization.

It is now known that immobilization related medical problems could be reduced or eliminated by early mobilization of the affected joint. It has been found to be advantageous to initiate joint mobilization immediately following orthopedic surgery, in many instances in the operating and recovery rooms while the patient is still under anesthesia. Specifically, continuous passive motion of the affected joints has been found to be effective in reducing or eliminating the above-referenced medical problems, promoting faster healing, reducing the amount of pain and medications, improving the range of movement of the affected joint after recovery, and the like.

Continuous passive motion devices (CPMs) are typically motor driven and are designed to exercise a particular joint by repeatedly extending and flexing the joint. CPMs are capable of applying continuous motion to the joint in a repeatable, consistent manner and can be adjusted to operate at different speeds and within a defined range of motion. In such CPMs, it is important that the joint be anatomically aligned on the CPM. The limb is typically supported on a moveable carriage member which is driven by the motor. The carriage member includes a plate or other straps or padding (generally referred to as "softgoods") for directly receiving the human limb. Straps or the like are used to secure a portion of the limb to the plate or softgoods. For instance, in the case of a CPM for a leg, usually only the foot is strapped to the CPM while the remaining portion of the leg merely rests on the soft goods.

The problem with a CPM for the leg that is not anatomically correct is that it does not maintain consistent axial alignment with the patient's hip, knee, and ankle joints through the range of motion of the patient's limb. This is because the axes of the CPM and the axes of the patient's hip, knee, and ankle do not match. The machine shifts position and the axis points shift because the CPM uses a hinge located under the patient's thigh near the base of the buttocks. Accordingly, the pivot axis is not in alignment with the hip.

CPMs which receive limbs in an anatomically correct manner are known. For instance, CPMs for the knee joint typically receive the leg of the patient such that the pivot axes of the knee and hip joints are aligned with the pivot axes of the CPM. Such CPMs usually include a pair of carriage members for receiving the thigh and calf. The carriage members are pivotally connected to each other at one end. The other end of the carriage members are pivotally connected to a base. Since the pivot axis of the thigh hip joint is in the pelvic region, it is difficult to align the pivot axis of the thigh carriage member therewith.

Conventionally, this problem has been resolved by providing the base with a cantilevered bar which extends from the proximal end of the base toward the pelvic region. The distal end of the bar pivotally receives the carriage member for supporting the thigh. The bar can be mounted on either lateral side of the base to accommodate either the left leg or the right leg. While such CPMs achieve anatomical alignment, they are problematic in that the bar must be repositioned on the left or right side of the base to receive the limb to be exercised. That is, if the CPM was set up to exercise the right leg for a first patient and a second patient needed therapy for the left leg, the CPM would have to be dismounted and reassembled with the bar on the left lateral side of the base. This results in downtime between patients as well as creating unnecessary tasks for the therapists. Another problem is the cantilever effect places a great deal of stress on the CPM's proximal hinge. Yet, another problem is the overall length of existing anatomically correct CPMs. When the CPM aligns with the hip of the patient and the head of the hospital bed is raised, the mattress contacts the base of the hinge and pushes the CPM forward, trapping the CPM to the foot of the bed. Hence, a need has arisen for a bilateral CPM. That is, a CPM which can anatomically receive either a right limb or a left limb without the need to adjust the CPM in accordance with the particular limb to be rehabilitated.

Conventional CPMs are problematic in that the plate or softgoods for receiving the limb are rigidly secured to the carriage member and loosely receive the majority of the limb. That is, with respect to a leg, while a foot is strapped to the CPM, the thigh and calf rest loosely on the soft goods. Potentially, the patient could move or slip during the operation of the CPM and thereby cause the leg to move out of anatomical alignment with the CPM. As such, a need has developed for a CPM which securely receives the limb to prevent the same from moving out of anatomical alignment during the operation thereof.

Other CPMs have drawbacks in that they lack the requisite amount of power to raise and bend a relatively heavy limb. Many patients, such as a football player or perhaps a short nonflexible patient, can easily exceed the lifting capacity of conventional CPMs. Presently, this problem has been addressed by a machine which includes a large double reduction gear head that is supported by an external stand attached to the frame of a hospital bed. This machine exceeds seventy-five pounds in weight and is hard to move from patient to patient. Consequently, a need has arisen for a CPM which has the requisite power required to raise and bend a relatively heavy limb without increasing the overall size and weight of the CPM.

Conventional indirect drive CPMs drive one end of the carriage member at a substantially constant velocity. Because of the typical triangular configuration formed between the carriage member and base of the indirect drive CPMs, moving one end of the carriage member at a substantially constant velocity results in an varying angular velocity at the joint as it is repeatedly flexed and extended. Conventional CPMs are typically driven by electrically powered motors which have a speed that is directly proportional to the applied voltage and inversely proportional to the applied load. This usually results in speed variance that is inconsistent with patient comfort. Thus, a need has arisen for a CPM which can maintain constant angular velocity of the joint being treated.

The present invention overcomes many of the disadvantages inherent in the above-described CPMs by providing an anatomically correct CPM which is equally usable with both the right and left limbs thereof, thereby eliminating any downtime normally required to switch the CPM between right hand and left hand use. The present CPM is shorter than existing anatomically correct CPMs being approximately equal in length to non-anatomically correct CPMs. The present invention eliminates the need for a conventional thigh carriage and thus reduces the stress on the second hinge adjacent the patient's hip. The present invention flexes the joint at a constant angular velocity and is capable of lifting relatively heavy limbs. The present invention is also capable of achieving consistent anatomical alignment by firmly securing the limb to the CPM to prevent the patient's leg from shifting during therapy. Consequently, use of the present invention results in reduced downtime between patients, comfort to the patient, and enhanced rehabilitation of the joint.

SUMMARY OF THE INVENTION

Briefly stated, the present invention comprises an anatomically correct continuous passive motion orthosis device for a limb. The limb is formed by a first body portion having a first end and a second end, a second body portion having a first end and a second end, and a third body portion. The first end of the first body portion is pivotably joined to the second end of the second body portion to form a first joint such that the first body portion is pivotable with respect to the second body portion about a first joint pivot axis. The device comprises a base having a proximal end and a distal end, a first carriage member for receiving the first body portion of the limb, and a second carriage member for receiving the second body portion of the limb. The first and second carriage members have respective first and second ends. A first hinge means interconnects the second end of the first carriage member and the first end of the second carriage member such that the first carriage member is pivotable with respect to the second carriage member about a first support pivot axis. A drive means is interconnected between the base and the first carriage member for reciprocally moving the first carriage member between the distal and proximal ends of the base. A second hinge means is interconnected between the second end of the second carriage member and the base such that the second carriage member is pivotable about a second virtual support pivot axis; that is, an axis that is displaced from the second hinge's physical connection to the base. The second support pivot axis is aligned with the end of the second body portion (such as the hip) and is spaced from the second hinge means and the proximal end of the base. The first and second body portions are respectively positionable on the first and second carriage members such that the first and second joint pivot axes are generally aligned with the first and second support pivot axis, respectively. The first and second joint pivot axes and the first and second support pivot axes, respectively, remain aligned as the first carriage member moves back and forth between the distal and proximal ends of the base.

BRIEF DESCRIPTION OF THE DRAWINGS

The foregoing summary, as well as the following detailed description of the preferred embodiment, will be better understood when read in conjunction with the appended drawings. For the purpose of illustrating the invention, there is shown in the drawings an embodiment which is presently preferred, it being understood, however, that the invention is not limited to the specific methods and instrumentalities disclosed. In the drawings.

DESCRIPTION OF PREFERRED EMBODIMENT

Figure 1:
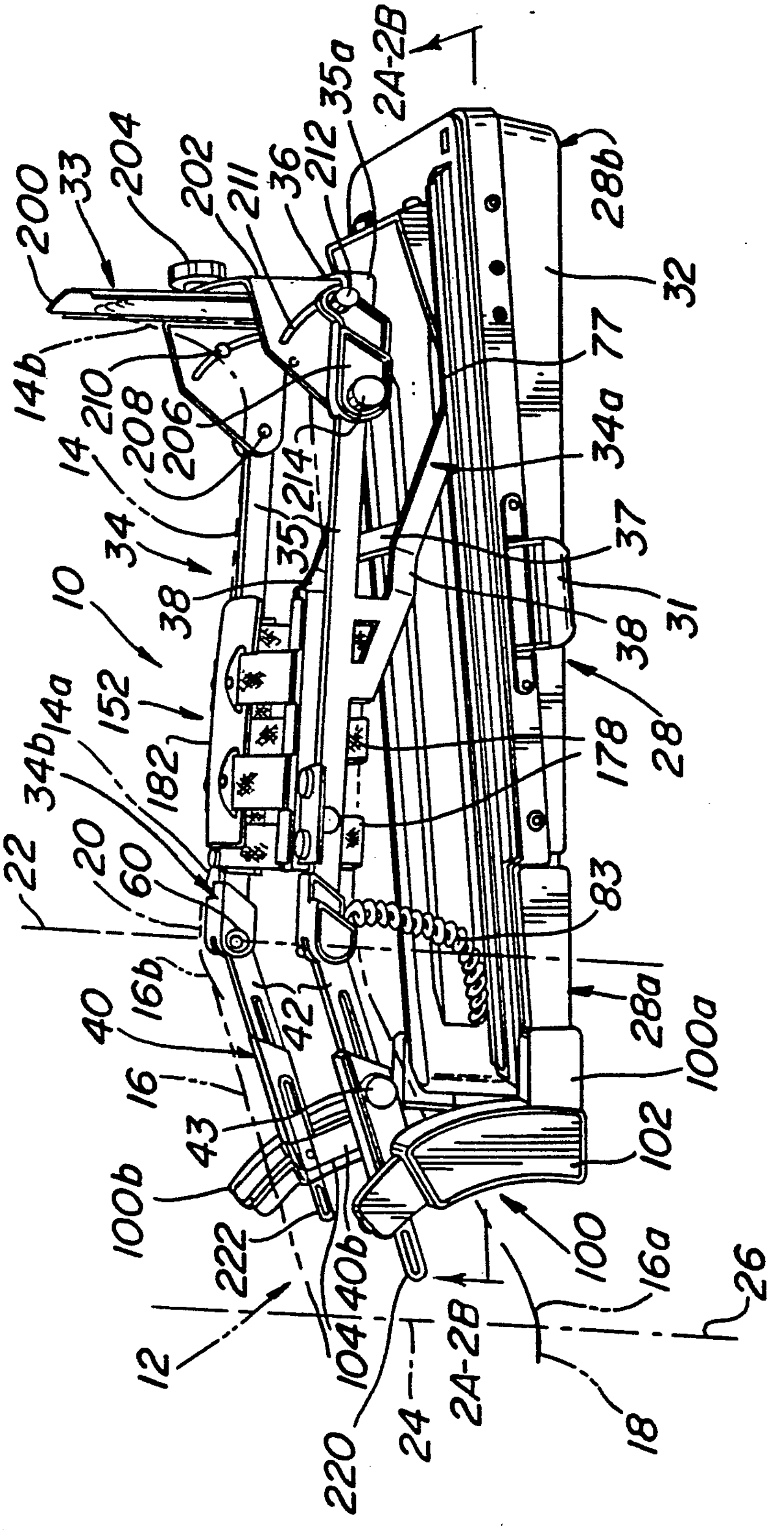
FIG. 1 is perspective view of a continuous passive motion orthosis device for a limb in accordance with the present invention.

Certain terminology is used in the following description for convenience only and is not limiting. The words "right," "left," "lower" and "upper" designate directions in the drawings to which reference is made. The words "inwardly" and "outwardly" refer to directions toward and away from, respectively, the geometric center of the CPM and designated parts thereof. The terminology includes the words above specifically mentioned, derivatives thereof and words of similar import.

Referring now to the drawings in detail, wherein like numerals indicate like elements throughout, there is shown in FIGS. 1 through 9 a preferred embodiment of an anatomically correct continuous passive motion orthosis device (CPM), generally designated 10, for a limb 12 (shown in phantom). It is preferred that the limb 12 be formed by a first body portion 14 having a first end **14*a* and a second end 14*b*, a second body portion 16 having a first end 16*a* and a second end 16*b*, and a third body portion 18. The first end 14*a* of the first body portion 14 is pivotally connected to the second end 16*b* of the second body portion 16 to form a first joint 20 such that the first body portion 14 articulates with respect to the second body portion 16 about a first joint pivot axis 22. The first end 16*a* of the second body portion 16 is pivotably connected to the third body portion 18 to form a second joint 24 such that the second body portion 16 articulates with respect to the third body portion 18 about a second joint pivot axis 26**.

In the present embodiment, the limb 12 is preferably a leg and the first and second joints 20, 24 are the knee and hip joints of the leg 12, respectively. Similarly, it is preferred that the thigh and calf and ankle of the leg correspond to the second and first body portions 16, 14. It is also understood by those skilled in the art that the present invention is not limited to any particular limb. For instance, the present invention is equally applicable to the arm or any other limb of the human body or subparts thereof, such as the wrist or elbow. Moreover, the present invention is not limited to limbs having joints with a particular number of pivot axes. For example, the limb could have a joint having one, two or three pivot axes without departing from the spirit and scope of the invention. Furthermore, it is understood by those skilled in the art that the present invention is equally applicable to nonhuman limbs, such as the leg of a monkey or ape.

Unless otherwise indicated herein, it is understood that all of the elements of the CPM 10 are preferably constructed of a high-strength, lightweight metallic material, such as aluminum. However, it is understood by those skilled in the art that the present invention is not limited to constructing the CPM 10 of any particular material and that the CPM 10 could be constructed of other high-strength lightweight materials, such as a composite fibrous and resin material or any suitable polymeric material.

Figure 2A:
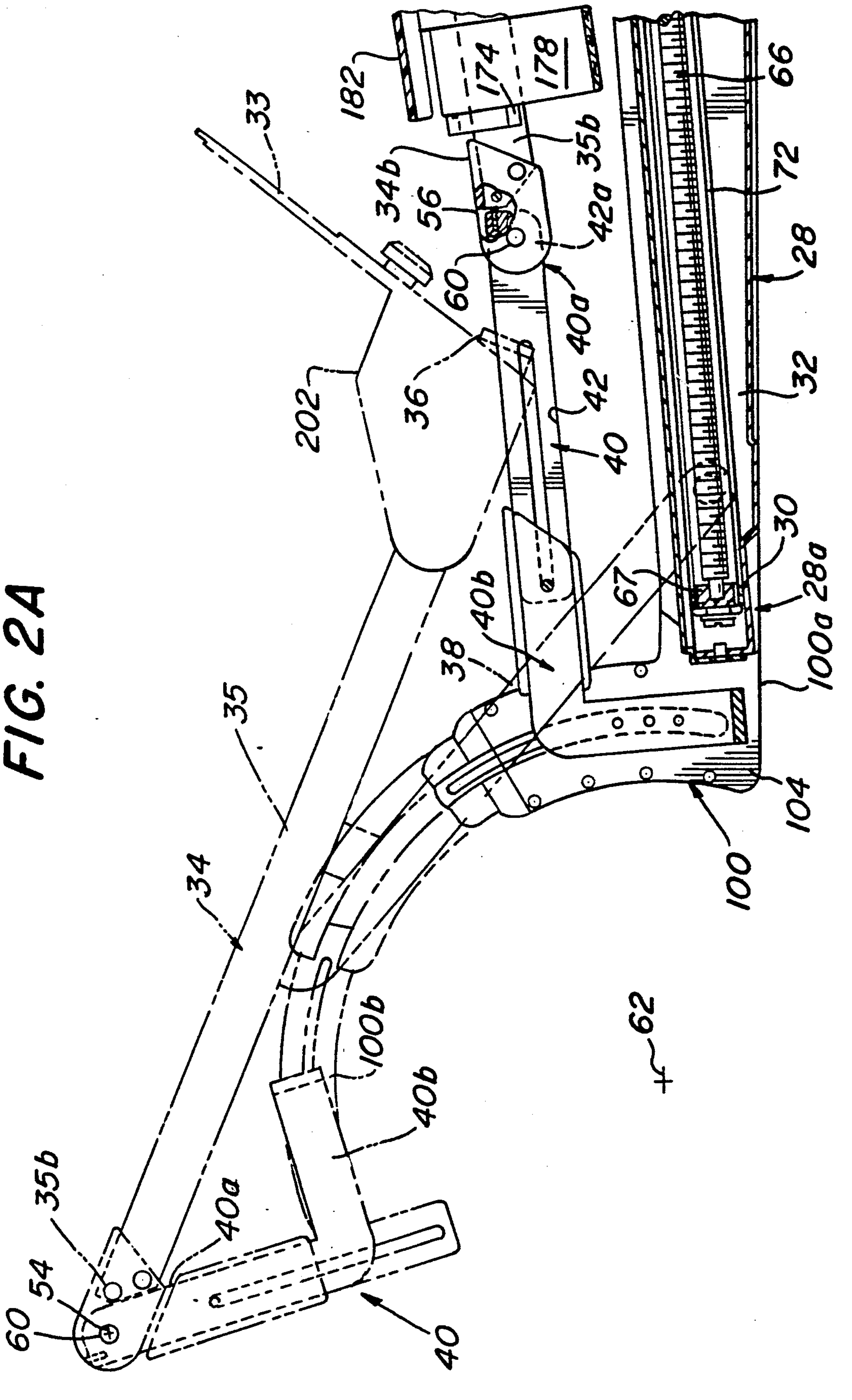
FIGS. 2A and 2B are a cross-section view of the device shown in FIG. 1 taken along line 2A—2B—2A—2B of FIG. 1.
Figure 2B:
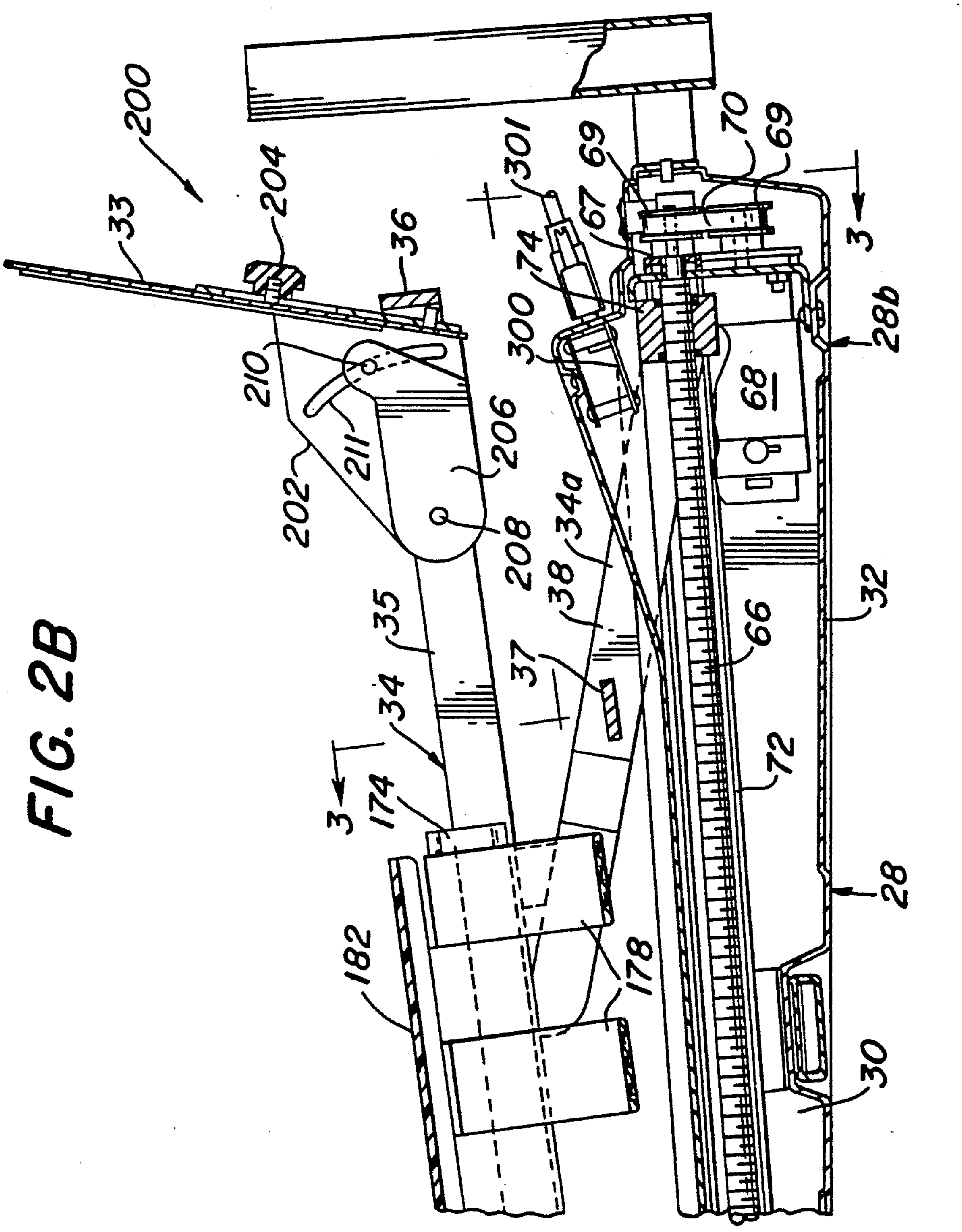

Referring now to FIGS. 1, 2A and 2B, the CPM 10 includes a base 28 having a proximal end 28*a* and a distal end 28*b*. In the present embodiment, the base 28 is preferably generally in the form of an elongate wedge. The base 28 includes a frame 30 (see FIG. 2A) for supporting the various elements of the CPM 10. The frame 30 is encompassed within a housing 32 for providing the CPM 10 with angular advantage and an overall aesthetically pleasing look. The housing 32 is preferably formed of upper and lower portions 32*a*, 32*b* (see FIG. 3) and is constructed of a suitable, moldable polymeric material, such as polyvinyl chloride, to decrease the overall weight of the CPM 10. The housing 32 includes a handle 31 for promoting the portability of the CPM 10. It is understood by those skilled in the art, that the housing 32 could be omitted or constructed of other materials, without departing from the spirit and scope of the invention, such as wood or a lightweight metallic alloy.

Referring now to FIG. 1, the CPM 10 includes a first carriage member 34 for receiving the first body portion 14 of the limb 12. The first carriage member 34 has a first end (or distal) 34*a* and a second end (or proximal) 34*b*. In the present embodiment, it is preferred that the first carriage member 34 be comprised of a pair of elongate spaced generally parallel side rails 35. The side rails 35 are preferably generally linear and are spaced a sufficient distance to complementarily receive the first body portion 14 of the limb 12. The side rails 35 are connected by a transversely extending cross member 36 at the distal ends 35*a* thereof. The side rails 35 include means for receiving the second end 14*b* of the first body portion 14. In the present embodiment, it is preferred that the means for receiving the second end 14*b* of the first body portion 14 be a footrest 33 which is slideably adjustable along the length of the side rails 35 and is tiltable to different angles with respect to the side rails 35. The side rails 35 include a proximal end 35*b* which forms the second end 34*b* of the first carriage member 34.

Referring now to FIGS. 1, 2A and 2B, the foot rest 33 includes an elongated foot bed 200 adjustably connected to a foot support member 202 by any conventional means such as a threaded rod and knob 204. The foot support member 202 is generally U-shaped in cross section with its side arms being held juxtaposed to the inside surface of the side rails 35. Each side arm is pivotably connected to a side 206 by means of pins 208 and 210. Each pin 210 has an enlarged head which extend through an arcuate slot 211 where it threadably engages a knob 212. By loosening the knob 212, the angle of the foot bed 200 with respect to the side rails 35 can be adjusted to a desired angle. Moreover, each slide 206 is adjustably positioned along a side rail 35 by loosening a knob and rod 214 threadably extending through a slide 206. Thus, the foot rest 33 can be positioned along the rails 35 to accommodate the length of a patient's first body portion 14 (e.g., the length of his/her lower leg from the knee to the ankle).

In the present embodiment, the ankle of the first body portion 14 is anatomically aligned on the foot rest 33. Anatomical alignment of the ankle joint on the foot rest 33 assists in maintaining the first and second joint pivot axes 22, 26 in alignment with the first and second support pivot axes 54, 62, respectively, as the first end 34*a* of the first carriage member 34 moves between the proximal and distal ends 28*a*, 28*b* of the base 28. If the ankle were not anatomically aligned, the first joint pivot axis 22 may move out of alignment with the first support pivot axis 54 during actuation of the CPM 10.

Referring now to FIGS. 1, 2A, 2B and 3, extending downwardly from the side rails 35 into the base 28 are a pair of corresponding support rods 38. The support rods 38 support the side rails 35 above the base 28 and include a cross member 37 extending transversely therebetween for providing the first carriage member 34 with structural integrity. The distal ends 38*a* of the support rods 38 form the first end 34*a* of the first carriage member 34, as described in more detail hereinafter.

As shown in FIG. 1, the CPM 10 further includes a second carriage member 40 for receiving the second body portion 16 of the limb 12. The second carriage member 40 has a first end (or distal) 40*a* and a second end (or proximal) 40*b*. The first end 40*a* of the second carriage member 40 is spaced from the second end 40*b* of the second carriage member 40 a predetermined distance. In the present embodiment, it is preferred that the second carriage member 40 be comprised of a pair of spaced generally parallel elongate support rails 42. The support rails 42 are preferably spaced a sufficient distance to complementarily receive the second body portion 16 therebetween. The carriage member 40, like the side rails 35, includes a cross rail 44 extending generally transversely between the support rails 42 for providing the same with structural integrity, see FIG. 5.

Figure 5:
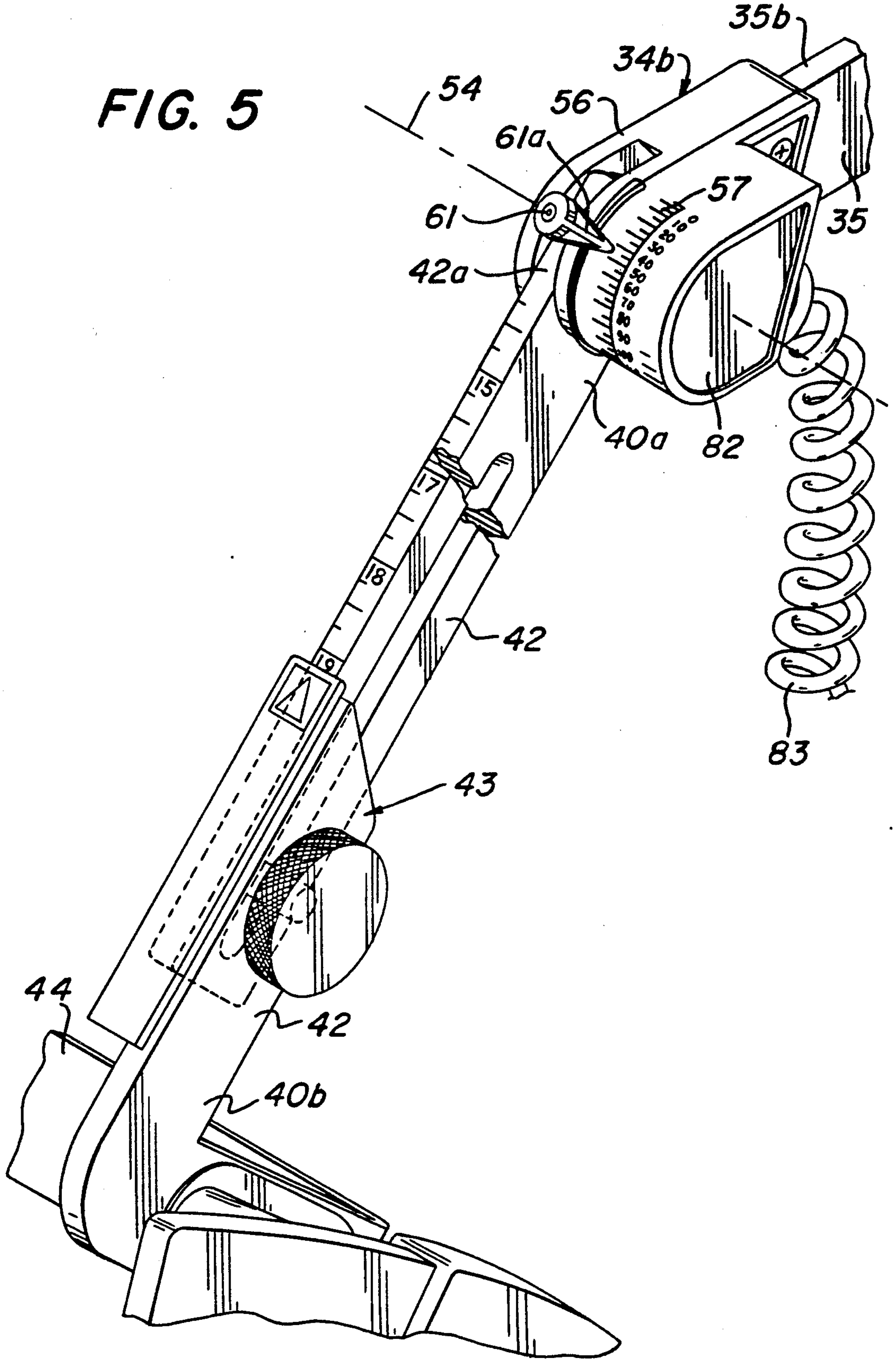
FIG. 5 is a greatly enlarged perspective view of an angle indicator for the device of FIG. 1.

Referring now to FIG. 5, each of the support rails 42 include length adjusting means for adjusting the distance between the first and second ends 40*a*, 40*b* of the second carriage member 40 to allow the CPM 10 to receive limbs of varying length. In the present embodiment, the length adjusting means is comprised of a bolt and slide mechanism 43 on the support rails 42 for allowing the support rails 42 to extend and contract to different lengths and to maintain the support rails 42 in alignment. The bolt and slide mechanism 43 is well understood by those skilled in the art and does not form any part of the present invention. Accordingly, further description thereof is omitted for purposes of convenience only and is not limiting.

Referring now to FIGS. 1, 2A and 5, a first hinge means is interconnected between the second end 34*b* of the first carriage member 34 and the first end 40*a* of the second carriage member 40 such that the first carriage member 34 is pivotable with respect to the second carriage member 40 about a first support pivot axis 54. In the present embodiment, the first hinge means is comprised of a yoke 56 extending from each of the proximal ends 35*b* of the side rails 35 for receiving a distal end 42*a* of the corresponding support rails 42 therein. The yokes 56 and distal ends 42*a* of the support rails 42 include an aperture extending therethrough and the same are positioned in registry for receiving a pin 60 to allow the first carriage member 34 to pivot with respect to the second carriage member 40. It is understood by those skilled in the art that the present invention is not limited to any particular means for allowing the first and second carriage members 34, 40 to pivot with respect to each other. For instance, the first end 40*a* of the second carriage member 40 could include a yoke (not shown) extending therefrom for receiving the second end 34*b* of the first carriage member 34.

Referring now to FIGS. 1 and 2A, the CPM 10 includes a second hinge means interconnected between the second end 40*b* of the second carriage member 40 and the proximal end 28*a* of the base 28 such that the second carriage member 40 is pivotable about a virtual second support pivot axis 62. The virtual second support pivot axis 62 is spaced from the second hinge means and the proximal end 28*a* of the base 28. More particularly, it is preferred that the virtual second support pivot axis 62 be spaced from the second hinge means and the proximal end 28*a* of the base member 28 a distance sufficient to permit the axis 62 to be aligned with the second joint. For a knee CPM this is the hip; and for an adult, it is chosen to be approximately 10.83 inches behind the frame 30 at the proximal end 28*a* of the base member 28. Accordingly, the CPM 10 can be readily used with the limb 12 and a symmetrical opposite side limb (not shown). Thus, the CPM 10 of the present invention is bilateral. Moreover, its overall length is essentially the same as that of a nonanatomically correct CPM.

Figure 6:
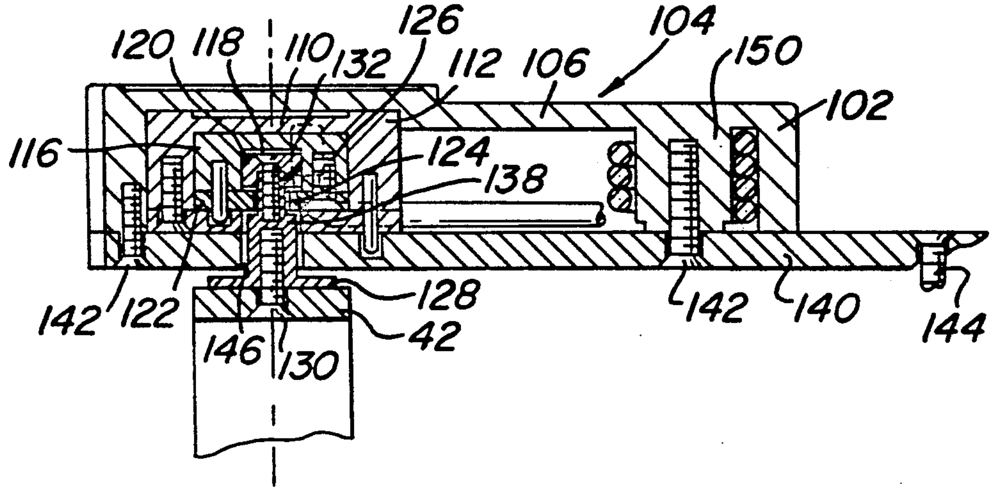
FIG. 6 is a greatly enlarged cross-sectional view of the telescopically expanding hinge shown in FIG. 4, taken along line 6—6 of FIG. 4.
Figure 4:
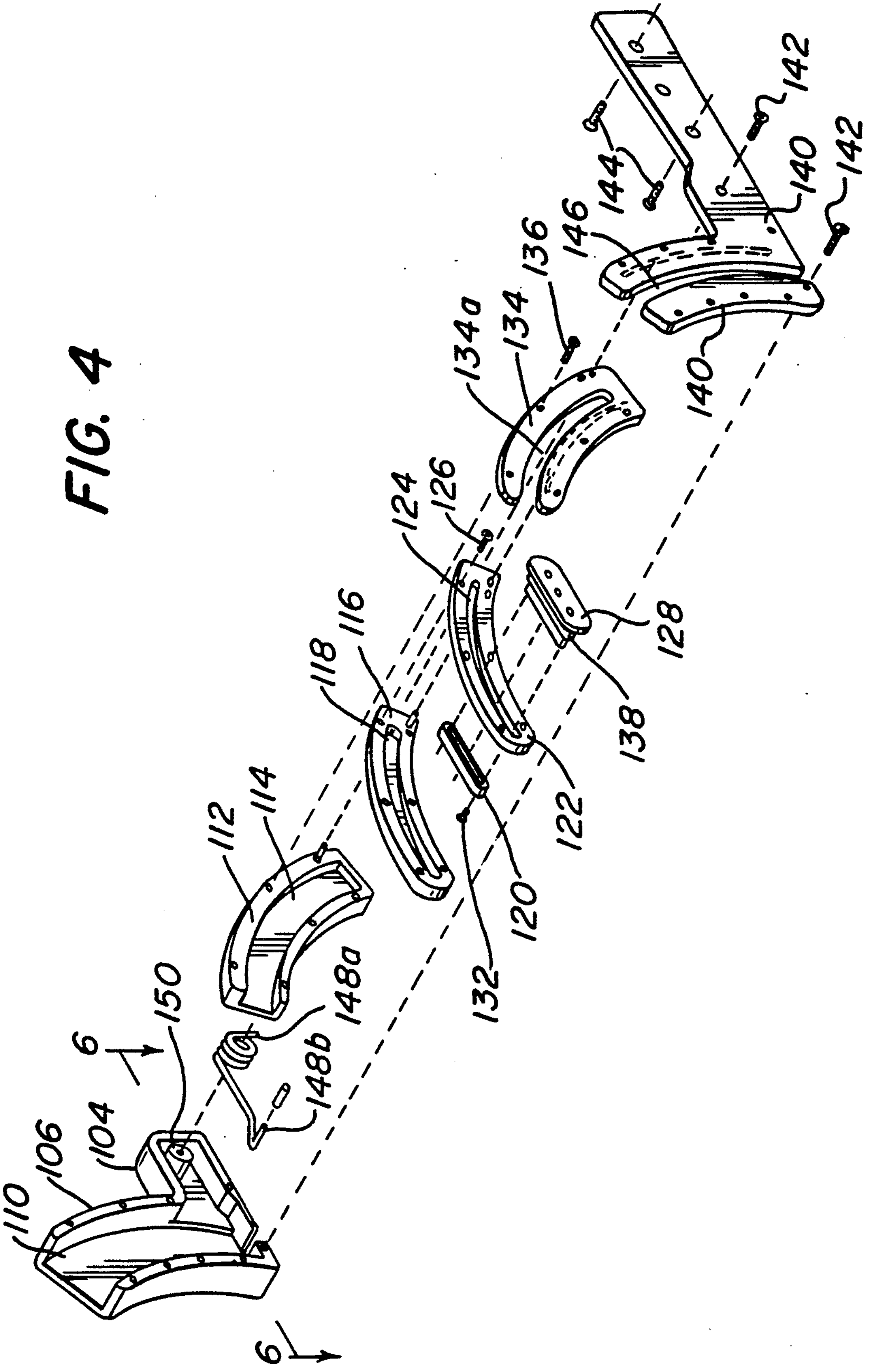
FIG. 4 is an exploded perspective view of a telescopically expanding hinge for the device shown in FIG. 1.

Referring now to FIGS. 2A, 4 and 6, in the present embodiment, it is preferred that the second hinge means be comprised of a radially expanding assembly 100 having a first end 100*a* fixed to the frame 30 at the proximal end 28*a* of the base 28 and a second end 100*b* fixed to the second end 40*b* of the second carriage member 40 such that the second end 100*b* of the assembly 100 moves accurately away from the first end 100*a* of the assembly 100 as the first carriage member 34 moves from the distal end 28*b* of the base 28 to the proximal end 28*a* of the base 28 and the second end 100*b* of the assembly 100 moves accurately towards the first end 100*a* of the assembly 100 as the first carriage member 34 moves from the proximal end 28*a* of the base 28 to the distal end 28*b* of the base 28, as described in more detail hereinafter. As best shown in FIG. 2A, it is preferred that the assembly 100 expand telescopically along an arcuate path. The preferred radius at the center line of the arc is eight and one quarter inches so the virtual axis 62 aligns with a patient's second joint (i.e., the hip when the patient is an adult lying prone on his/her back).

Referring now to FIGS. 1, 4 and 6 the assembly 100 is preferably comprised of a first subassembly 102 and a second subassembly 104. Each subassembly 102, 104 is interconnected between the frame 30 at the proximal end 28*a* of the base 28 and one of the support rails 42. The second subassembly 104 is shown in FIGS. 4 and 6 and includes a generally L-shaped jacket 106. It is preferred that the jacket 106 be generally hollow and include a generally arcuate slot 110. Positioned within the slot 110 is a first expanding member 112. The first expanding member 112 is configured to complement the slot 110 of the jacket 106 to allow the same to reciprocate within the slot 110 along the arcuate path. The first expanding member 112 also includes an arcuate slot 114 on the surface thereof. The slots 110 and 114 are preferably generally closed on one end and open on the other for permitting contained telescopic expansion, as described in more detail hereinafter.

A second expanding member 116 is slideably disposed within the slot 114 of the first expanding member 112. It is preferred that the second expanding member 116 be configured to complement the slot 114 of the first expanding member 112 to permit the second expanding member 116 to expand telescopically through the open end of the slot 114. The second expanding member 116 also includes an arcuate slot 118 for receiving a follower member 120. The slot 118 of the second expanding member 116 is also generally arcuate and complementarily configured to correspond to the configuration of the follower member 120. Thus, the follower member 120 is slideably disposed within the slot 118 of the second expanding member 116. The second expanding member 116 includes a cover 122 having a slot 124 disposed therethrough which complements the configuration of the slot 118 of the second expanding member 116. The cover 122 is secured to the second expanding member 116 by a series of standard fasteners, such as screws 126.

A connecting member 128 is secured to the follower member 120 and the support rail 42 by standard fasteners, such as screws 130, 132, as shown in FIG. 6. The second expanding member 116 and the cover 122 are positioned entirely within the slot 114 of the first expanding member 112. A cover 134 is positioned over the slot 114 and secured in place by a series of screws 136. The connecting member 128 includes stepped portions 138 which extend through a slot 134*a* in the cover 134 and allow the connecting member 128 to be positioned externally of the cover 134 and first expanding member 112. The assembled first expanding member 112 is positioned within the slot 110 of the jacket 106 in a complementary fashion to permit the first expanding member 112 to be slideably disposed therein. A cover 140 is disposed over the slot 110 of the jacket 106 to securely retain the first and second expanding members 112, 116 therein. The cover 140 is secured to the jacket 106 by standard fasteners, such as screws 142. The cover 140 is in facing engagement with the frame 30 retained within base 28 and is secured thereto by a plurality of screws 144 which extend through the cover 140. The connecting member 128 is also disposed through a slot 146 in the cover 140 for permitting the same to reciprocate therein.

In the present embodiment, the first subassembly 102 is generally identical to the second subassembly 104 except that it is a mirror image thereof. Accordingly, further description of the first subassembly 102 is omitted for purposes of convenience only and is not limiting. While it is preferred that the expanding assembly 100 be comprised of two subassemblies 102, 104, it is understood by those skilled in the art that a single subassembly could be used without departing from the spirit and scope of the invention. Similarly, while it is preferred that the subassemblies 102, 104 provide for three stage telescopic expansion, it is understood by those skilled in the art that any number of telescopic stages of expansion can be used such as two or four, without departing from the spirit and scope of the invention. While in the present embodiment it is preferred that the first and second subassemblies 102, 104 be assembled by standard fasteners, such as screws, it is also understood by those skilled in the art that other means could be used to assemble the same, such as rivets or an adhesive. Similarly, it is understood by those skilled in the art that portions of the subassemblies 102, 104 could be molded as on part. For instance, the first and second expanding members 172, 176 and the associated covers 122, 134 could be molded as one part, to obviate the need for the screws.

As best shown in FIG. 1, the first and second body portions 14, 16 are respectively positionable on the first and second carriage members 34, 40 such that the first joint pivot axis 22 is generally aligned with the first support pivot axis 54 (FIG. 5).

The first carriage member 34 includes securing means mounted thereon for receiving and securing the first body portion 14 of the limb 12 to the first carriage member 34 to help retain the limb 12 on the first and second carriage members 34, 40 and maintain the first and second joint pivot axes 22, 26 and the first and second support pivot axes 54, 62, respectively, aligned as the first carriage member 34 moves between the distal and proximal ends 28*b*, 28*a* of the base 28, as described in more detail hereinafter.

Figure 3:
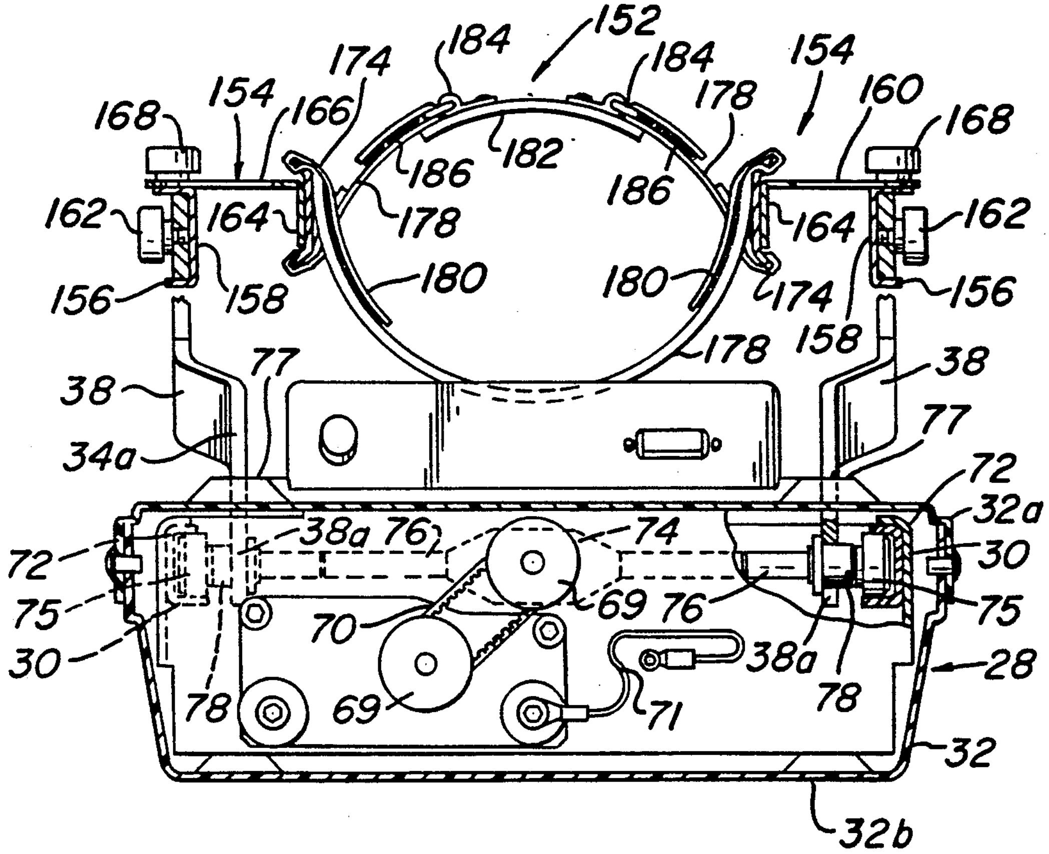
FIG. 3 is a cross-sectional view of the device shown in FIG. 1 taken along line 3—3 of FIG. 2B.
Figure 7:
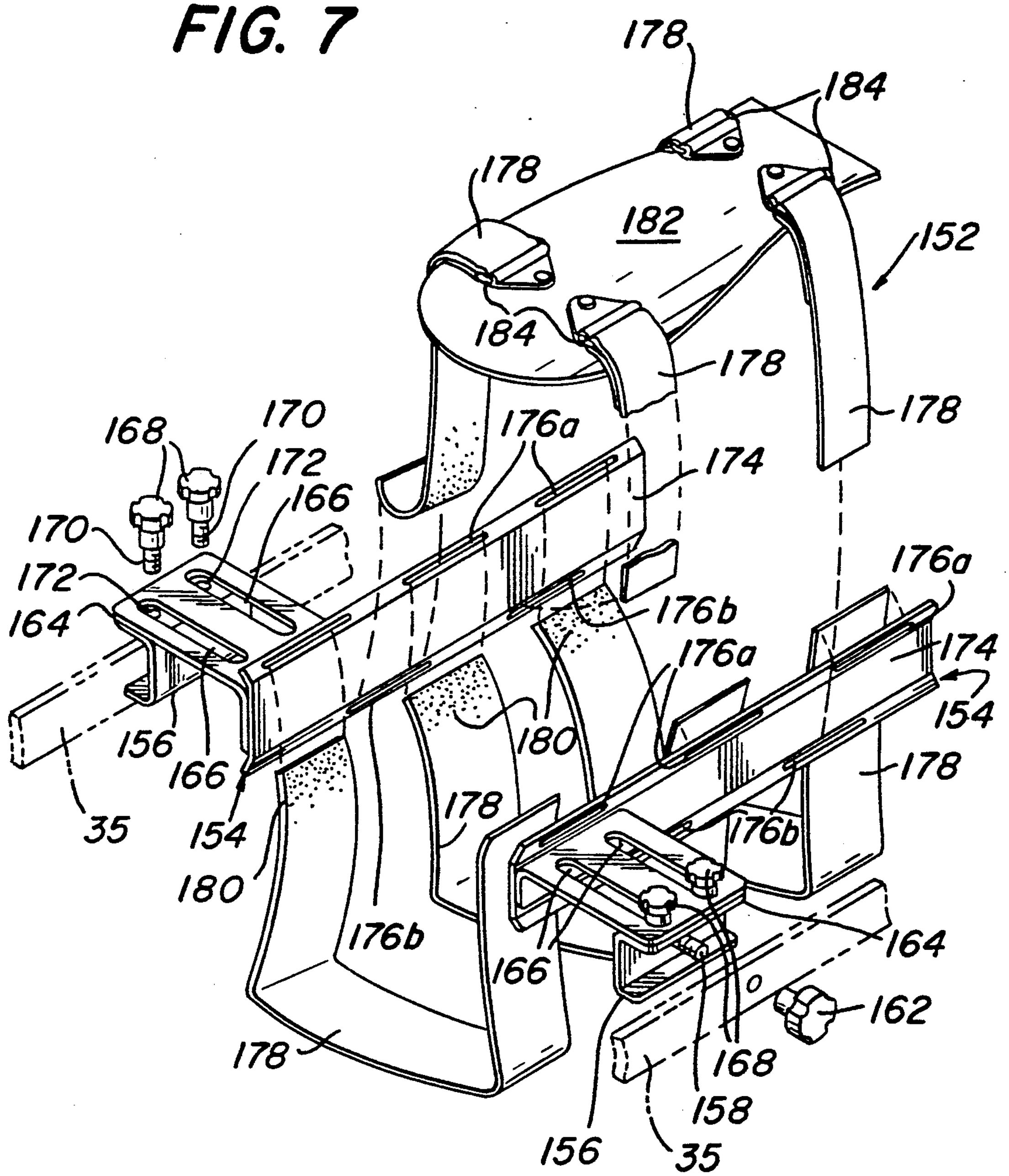
FIG. 7 is a greatly enlarged exploded perspective view of a knee extention system for the device shown in FIG. 1.

Referring now to FIGS. 1, 3 and 7, in the present embodiment, it is preferred that the securing means be comprised of a knee extention system 152 which secures the limb 12 to the first carriage member 34. The knee extention system 152 is comprised of a pair of complementary adjustable mounting assemblies 154. Each mounting assembly 154 includes a U-shaped channel 156 which is correspondingly sized to receive a side rail 35 therein. The U-shaped channel 156 includes a bolt 158 for being positioned through a complementary aperture 160 in the corresponding side rail 35. A threaded knob 162 receives the bolt 158 to secure the mounting assembly 154 to the side rail 35.

An L-shaped bracket 164 extends from the U-shaped channel member 156. One leg of the L-shaped bracket includes a pair of elongate slots 166. Extending through the slots 166 are a pair of adjusting knobs 168 which include a threaded bolt 170 extending therefrom and through one of the slots 166 into a complementarily threaded aperture 172 located in the U-shaped channel 156. Secured to the other leg of the L-shaped bracket 164 by welding or the like is a limb supporting channel 174. The position of the limb supporting channel 174 is adjustable with respect to the U-shaped channel 156 by tightening and loosening the adjusting nuts 168 and sliding the L-shaped bracket 164 with respect to the U-shaped channel 156 to move the limb supporting channel 174 towards and/or away from the side rail 35. By adjusting both limb supporting channels 174 to the appropriate distance therebetween, the CPM 10 can be adjusted to receive different size limbs 12 and to position the limb based on individual anatomical limits.

As best shown in FIGS. 3, 5 and 7, the limb supporting channel 174 includes three upper slots 176*a* and two lower slots 176*b*, respectively. Each of the upper slots 176*a* receive a strap 178 therethrough which is wrapped over and secured to itself by hook and loop material 180. When all three of the straps 178 which extend through the upper slots 176*a* are in place, the limb 12 can be rested thereon. To firmly secure the limb 12 to the straps 178 extending through the upper slots 176*a*, a contoured plate 182 is secured to the limb 12 and held in position by the straps 178 which extend through the lower slots 176*a*. The plate 182 is held in place by wrapping the straps through the loops of the fasteners 184 on the upper surface thereof and laying the strap over itself to engage the hook and loop material 186.

While in the present embodiment, it is preferred that the limb 12 be secured to the first carriage member 34 by the knee extention system 152, it is understood by those skilled in the art that other devices can be used for securing the limb 12 to the first carriage member 34.

Thus, the knee extention system 152 holds a patient's calf and ankle in position so that the knee pivot axis remains aligned with the CPM pivot axis 54.

As shown in FIG. 1, support and positioning for the second body portion 16 (e.g., the thigh) on the second carriage member 40 is provided by pivot plates 220 pivotally attached to the inside surface of subassemblies 102, 104. Plates 220 include elongated openings 222 for receiving straps (not shown) for retaining the second body portion 16 in position on the second carriage member 40. Since the pivot plates 220 are pivotably connected to the second carriage member 40, the second body portion 16 can independently rotate relative to the support rails 42. Thus, the pivot axis 54 remains aligned with the first joint pivot axis 22 according to the anatomical movement of the patient's limb 12. Stops for holding the second body portion 16 in position on the second carriage member 34 may include hook and loop fasteners. All limb retention devices are provided with softgoods in the form of padding as is conventional.

Referring now to FIGS. 2A, 2B and 3, there is shown drive means interconnected between the base 28 and the first end 34*a* of the first carriage member 34 for reciprocally moving the first end 34*a* of the first carriage member 34 between the distal and proximal ends 28*a*, 28*b* of the base 28. In the present embodiment, it is preferred that the drive means be comprised of an elongate screw 66 disposed within the frame 30 along the longitudinal axis thereof. The ends of the screws 66 are mounted within bearings 67 secured to the frame 30 for permitting the screw 30 to rotate about its longitudinal axis.

As best shown in FIG. 2B, at the distal end 28*b* of the base 28, within the housing 32, is a motor 68 which is drivingly connected to the screw 66 for rotation thereof. In the present embodiment, it is preferred that the motor 68 be spaced from and drivingly connected to the screw 66 by a pair of pulleys 69 and an endless toothed belt 70 to achieve a ratio of one-to-one. However, it is understood by those skilled in the art that the motor 68 could be connected to the screw 66 in other manners and mechanical advantage ratios without departing from the spirit and scope of the invention. For instance, the motor 68 could be directly connected to the elongate screw 66 to transfer torque between the motor 68 and the screw 66. The frame of the motor 68 is preferably electrically grounded to the frame 30 by a conductor 71 interconnected therebetween.

Referring now to FIGS. 2A, 2B and 3, disposed along the lateral edges of the base 28 are a pair of elongate channels 72 which are generally U-shaped in cross section. The channels 72 are preferably generally of the same length as the screw 66 and are positioned in spaced parallel relationship. The channels 72 are preferably formed as part of the frame 30. A complementary drive nut 74 is mounted on the screw 66. A pair of guidebars 76 extend outwardly from the nut 74 and include bearings 75 on the ends thereof which are in complementary rolling or sliding engagement with the channels 72. The guidebars 76 prevent the nut 74 from rotating with respect to the frame 30 and base 28. Consequently, when the motor 68 rotates the screw 66, the nut 74 reciprocates between the distal and proximal ends of the screw 66, as described in more detail hereinafter.

As best shown in FIG. 3, the first end 34a of the first carriage member 34 is secured to the guidebars 76 such that as the guidebars 76 reciprocate between the proximal and distal ends 28a, 28b of the base 28, the first carriage member 34 travels therewith. More particularly, the support rods 38 of the carriage member 34 extend downwardly through elongate slots 77 into the housing 32 and are pivotably secured to the guidebars 76 to allow the support rods 38 to rotate with respect to the guidebars 76 as they reciprocate between the proximal and distal ends 28a, 28b of the base 28. In the present embodiment, it is preferred that the guidebars 76 be generally circular in cross section for being positioned through a complementary aperture and bearing assembly 78 in the support rods 38 for allowing the support rods 38 to rotate with respect to the guidebars 76.

It is understood by those skilled in the art that other transmission devices can be used to transfer the torque of the motor 68 to the first carriage member 34. For instance, a rack and pinion arrangement (not shown) could be used in place of the screw 66 and nut 74 without departing from the scope of the invention.

Referring now to FIGS. 4 and 6, the base 28 includes biasing means for normally biasing the assembly 100 to an expanded position to assist the drive means or motor 68 in moving the first end 34a of the first carriage member 34 from the distal end 28b to the proximal end 28a of the base 28. In the present embodiment, it is preferred that the biasing means be comprised of a torsion spring 148 positioned within each subassembly 102, 104. With respect to the second subassembly 104, it is preferred that the torsion spring 148 be positioned over a complementary boss 150 within the jacket 106. One end 148a of the torsion spring 148 is engaged with the jacket 106 and the other end 148b applies pressure to the bottom surface of the first expanding member 112. A cover 140 is positioned over the other end 148b of the torsion spring 148 to firmly engage the first expanding member 112. The torsion spring 148 is preferably positioned within the jacket 106 to bias the first expanding member 112 upwardly through the slot 110 to assist the drive motor 68 in moving the first end 34a of the first carriage member 34 from the distal end 28b to the proximal end 28a of the base 28. The torsion spring 148 within the first subassembly 102 is generally identical to the torsion spring 148 in the second subassembly 104 except that it is a mirror image thereof and, therefore, further description thereof is omitted for purposes of convenience only and is not limiting.

In the present embodiment, it is preferred that each torsion spring 148 have a torque equivalent to approximately 81 inch/lbs. about the center of the torsion spring coil to thereby provide net lifting capacity of approximately thirty-five pounds at one foot from the second support pivot axis 62. It is understood by those skilled in the art that the combined strength of the torsion springs 148 can be different in accordance with the desired parameters of the CPM 10. It is also understood by those skilled in the art that a single torsion spring 148 could be utilized as opposed to two. Similarly, other means can be provided for expanding the assembly 100 to assist the drive means or motor 68 in moving the first end 34a of the first carriage member 34 from the distal end 28b to the proximal end 28a of the base 28, especially when the first end 34a is adjacent the distal end 28b of the base 28. For instance, a leaf spring (not shown) could be interconnected between the support rails 42 and the base 28.

Figure 8:
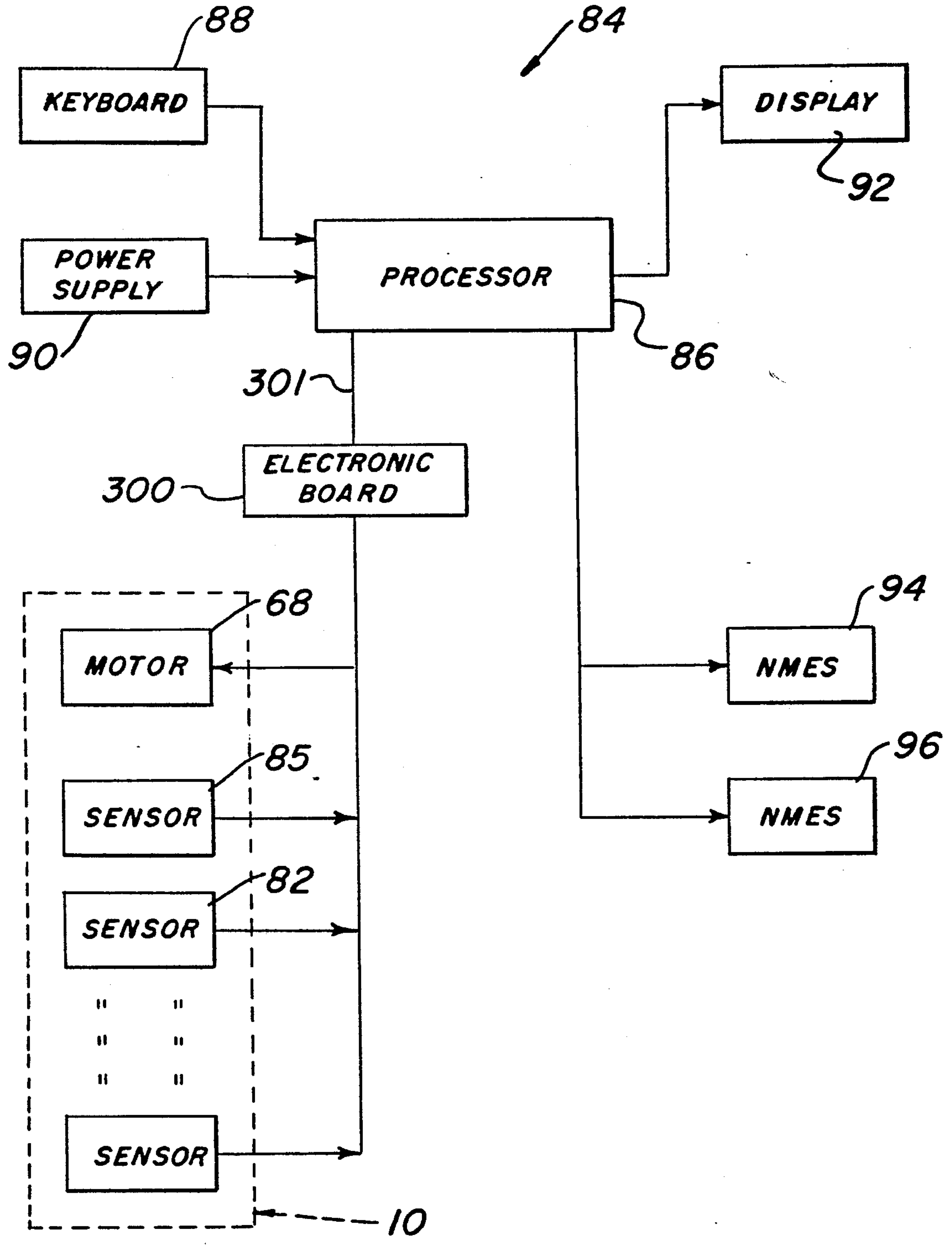
FIG. 8 is a block diagram of a control system for the device shown in FIG. 1 in accordance with the present invention.

Referring now to FIG. 8, the drive means includes speed control means for controlling the velocity of the first carriage member 34 along the base 28 between the distal and proximal ends 28b, 28a thereof, such that the first carriage member 34 pivots about the first support pivot axis 54 with respect to the second carriage member 40 at a predetermined angular velocity. That is, the angular velocity remains constant throughout the range of motion of the CPM 10. In the present embodiment, it is preferred that the speed control means include angular velocity determining means for determining the relative angular velocity between the first and second carriage members 34, 40 as the first and second carriage members 34, 40 pivot about the first support pivot axis 54.

Figure 9:
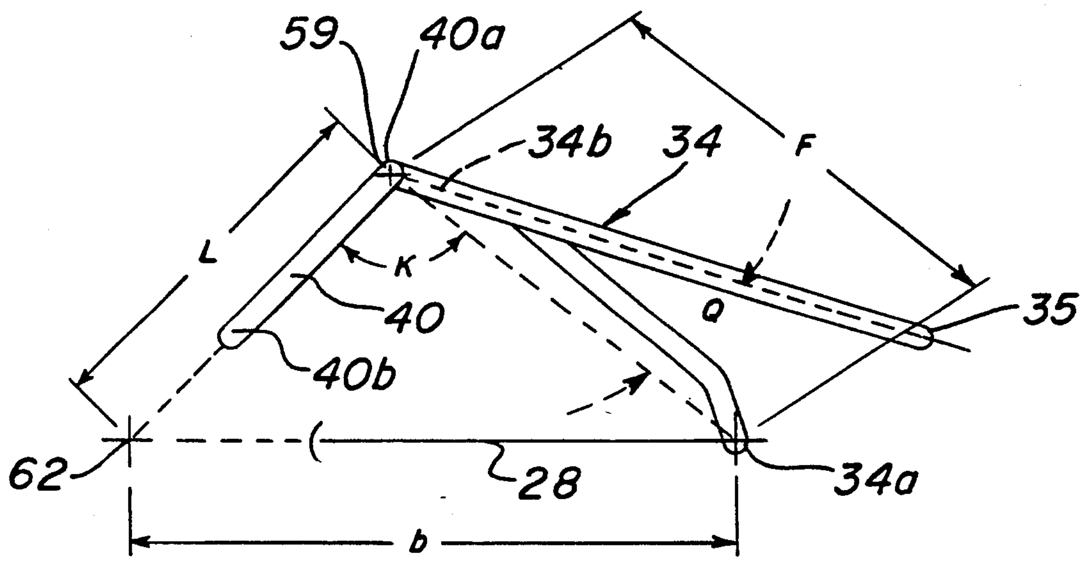
FIG. 9 is a schematic elevational view of the carriages of FIG. 1.

As shown in FIGS. 8 and 9, a sensor is positioned on the second carriage member 40 for determining the relative angular position of the first carriage member 34 with respect to the second carriage member 40 about the first support pivot axis 54. In the present embodiment, the sensor is comprised of an angular potentiometer 82. As shown in FIG. 5, the angular potentiometer 82 is secured to the yoke 56 on the proximal end 35b of the side rails 35. Angular potentiometers are well known to those skilled in the art. Accordingly, further description thereof is omitted for purposes of convenience only and is not limiting. The angular potentiometer 82 is in electrical communication through a wire 83 with a control unit, generally designated 84, which allows the therapist to control the operation of the CPM 10.

Referring now to FIG. 5, the angular potentiometer 82 also includes an angle indicator strip 57 adhesively secured to the face thereof. The angle indicator strip 57 includes a series of marked gradations which correspond to the angular position of the first carriage member 34 with respect to the second carriage member 40. A pointer 61 extends radially outwardly from the distal end 42a of the support rail 42 between the legs of the yoke 56. The pointer 61 includes a transversely extending finger 61a which overlaps the angle indicator strip 57. The position of the finger 61a with respect to the angle indicator strip 57 provides the therapist and/or patient with visual feedback regarding the angle of the first joint 20.

In addition to receiving signals from the angular potentiometer 82, the control unit 84 receives signals from a speed sensor 85 within the motor 68 which corresponds to the actual speed of the motor 68. The speed sensor 85 is preferably comprised of an optical encoder (not shown) on the armature (not shown) of the motor 68. The optical encoder provides a square wave type pulse train for motor speed feedback. The encoder sends the pulse train to an electronic board 300 (see FIG. 2B) which transmits the signals via a control cable 301 to the control unit 84. The electronic board 300 comprises two integrated circuits. The first integrated circuit contains a voltage regulator which is connected to a 5-volt power input pin located on the control unit 84. The second integrated circuit contains an H-bridge motor driver chip which acts as a switch and is connected to the motor leads. The motor driver chip determines the direction in which the motor is rotating. The motor drive chip also acts as an on/off switch such that the motor is controlled by pulse width modulation. In addition, a safety switch is connected to the motor leads so that in the case of certain fault detections, the motor is automatically shut off.

The control unit 84 includes a microprocessor 86 for receiving signals from the angular potentiometer 82 and the speed sensor 85 associated with the motor 68. The microprocessor 86 includes programming which correlates the signals from the angular potentiometer 82 and speed sensor 85 and controls the amount of power applied to the motor 68, and thus the speed of the same. In the present embodiment, it is preferred that the control unit 84 include an input device for inputting information into the microprocessor 86 which corresponds to the therapist's desired operation of the CPM 10. In the present embodiment, it is preferred that the input device be a keyboard or keypad 88, as is understood by those skilled in the art.

The microprocessor 86 is powered by a standard power supply 90. To confirm that the desired operating characteristics are input correctly and to display operational data (e.g. speed, range of motion, etc.), the control unit 84 is provided with a display 92, such as a liquid crystal display. It is understood by those skilled in the art that other displays could be used, such as a LED or a printer (not shown).

The microprocessor 86 is programmed to provide comparing means for comparing actual angular velocity with the predetermined or desired angular velocity inputted into the control unit by the therapist or to a default predetermined velocity if desired velocity is not inputted into the control unit 84 as stored within a table within the microprocessor 86. The angular velocity is preferably in the range of 10°/min to 120°/min. The actual angular velocity is ascertained by the microprocessor 83 which analyzes the signals from the angular potentiometer 82 over time. The microprocessor 86 adjusts the velocity of the first carriage member 34 along the base 28 if the determined velocity is different than the predetermined angular velocity by a preset limit, as determined by tables stored within the microprocessor. The velocity of the first carriage member 34 is adjusted such that the determined velocity is substantially equal to the predetermined angular velocity.

More particularly, the velocity of the first carriage member 34 is controlled by pulse width modulation of the power supplied to the motor 68 in response to motor speed and angular position feedback from the speed sensor 85 and angular potentiometer 82. The power ON pulse width is set by the tachometer pulse indicating that the motor is in motion. The OFF pulse width is set by a transfer function that uses tachometer count during the previous OFF period, present angular position, and the desired angular velocity. The control of the ON pulse assures that sufficient power is applied to overcome inertia, friction and motor reflective load. During the OFF period, the tachometer count provides an indication of motor coast which compensates for varying loads. Angular position feedback compensates for the trignometric relationship of motor speed to controlled joint angular velocity. The desired speed as determined by the user sets the nominal OFF period. Direct reading of angular position with appropriate scaling and averaging assures motions within set limits.

The present embodiment is an indirect drive orthosis device. Thus, movement of the first carriage member 34 causes a change in length of the distance along the base 28 between the first end 34*a* of the first carriage member and the virtual pivot axis 62 of the second carriage member, as shown in FIG. 9. The carriage members 34, 40 form a triangle defined formed by the length of the base b between the first end 34*a* of the first carriage member 34 and the virtual pivot axis 62 of the second carriage member 40, a leg frame F which corresponds to the linear distance between the first and second ends 34*a*, 34*b* of the first carriage member 34, and the thigh length L which corresponds to the linear distance between the first end 40*a* of the second carriage member 40 and the virtual pivot axis 62. In this configuration, at constant motor speed, the angular velocity at low knee angles K (e.g., 15° to 0°) can be significantly higher than at relatively high knee angles K. This results in a feeling that the knee is in a free-fall with no support from the CPM device. This is uncomfortable and sometimes painful to the patient. In the present invention the angular velocity between the first and second carriage members 34, 40 about the first support pivot axis 54 remains relatively constant by human perception and results in comfortable motion with constant CPM support. This is derived as a derivative of the base length b as a function of angular position resulting in the expression of base length velocity for constant angular velocity, normalized to leg frame dimensions.

Referring now to FIGS. 8 and 9, the following is a description of the calculations that the microprocessor 86 should perform to derive the desired velocity of the first end 34*a* of the first carriage member 34 along the base 28 to achieve constant angular velocity at the first joint 20. The following equation correlates incremental change in the base length b to an incremental change in the angular position K of the first and second carriage members 34, 40 at joint 20:

$$\frac{db}{dt} = \frac{L/F \operatorname{Sin}(K+Q)}{\sqrt{(L/F)^2 + 1 + 2\,L/F \operatorname{Cos}(K+Q)}} \;\; \frac{dk}{dt} \qquad (1)$$

where

K=angle between first and second carriage members 34, 40 at first support axis 54

Q=drive angle between the side rails 35 and the line extending between the first support pivot axis 54 and the first end 34*a* of the first carriage member 34

L=linear length of second carriage member 40 extended to the virtual pivot axis 62

F=linear length of first carriage member 34 (base to axis 54)

b=base length 28 extended to the virtual pivot axis 62

The first derivative of this equation yields the desired velocity of the first end 34*a* of the first carriage member 34 to achieve constant angular velocity (dk/dt) at the first joint 20 of the limb 12. However, such an equation would be too cumbersome for the microprocessor 86 to calculate. Therefore, it is preferred to develop constants which are based on the specific geometric configuration of the CPM 10 to simplify the calculation process. In the preferred embodiment, the distance F is equal to approximately 24.2 inches and the distance L is equal to approximately 14.3 to 19.7 inches, depending on the length of the second body portion 16. For purposes of simplicity, the distance L is always assumed to be 17.0 inches. Through empirical studies, a linearized constant was developed from the slope of the velocity curve to thereby yield the following less cumbersome equation:

$$db = L/F\,(K+Q+AK)/(B+AK) \quad (2)$$

where A and B are constant based upon the slope of the empirically derived velocity curve.

db, L, F, K, Q are the same as in equation (1).

For a CPM where L=14.3 to 19.7" and F is 24.2" as in the preferred embodiment of the present invention, equation (2) becomes $$b = 17.0/24.2\,(K+Q+19)/(128+19)$$

The value Q is a constant 13° and the value K is derived from the signals of the angular potentiometer 82 as well as standard trignometric derivations, understood by those skilled in the art. The values 128 and 19 were developed through empirical analysis. Thus, L is chosen to be 17" which is an approximate mid-length of the second carriage member 40 extended to the virtual pivot axis 62. The above equation yields the change in velocity of the first end 34a of the first carriage member 34 to achieve a sufficient constant angular velocity at the first joint 20 such that the patient will not experience the feeling of free fall during extension of the limb 12.

Referring now to FIG. 8, the CPM 10 of the present embodiment can further include a pair of neuro-muscular stimulators (NMES). An NMES is an electronic device that attaches to the muscles of the limb 12 to stimulate muscle contraction or relaxation. A first NMES 9 is provided for stimulating a muscle of the limb 12 at a pause period implemented when the limb 12 is fully extended and a second NMES 96 is provided for stimulating a muscle of the limb 12 during a pause period implemented when the limb 12 is fully contracted. The therapist decides which muscles to stimulate into contraction or relaxation. Of course, the therapist could opt to omit the use of NMES' entirely. The CPM 10 can sense stroke completion of the first carriage member 34 by measuring the angle K between the first and second carriage members 34, 40 about the first support pivot axis 54 and comparing the same to the range of motion input into the control unit 84 by the operator or to a default value. Other means can be used to sense stroke completion of the first carriage member 34, such as an encoder (not shown) mounted on the screw 66 which can determine the position of the nut 74 and calculate the angle K. NMES' are well known to those skilled in the art and, therefore, further description thereof is omitted for purposes of convenience only and is not limiting.

It is understood by those skilled in the art that other methods or devices can be used to control the CPM 10. For instance, the controller described in the patent application Ser. No. 07/760,424 entitled "Universal Controller for Continuous Passive Motion Devices," filed Sep. 16, 1991, and assigned to the owner of this application, can be used to control the operation of the CPM 10 and his hereby incorporated by reference in its entirety.

In use, the patient is positioned proximate the CPM 10 with a limb 12 in engagement with the first and second carriage members 34, 40. The knee extention system 152, pivot plates 222 and associated limb securing means secures the first and second body portions 14, 16 of the limb 12 to the first and second carriage members 34, 40, respectively. The actual angular velocity is ascertained by the microprocessor 86 which analyzes the signals from the angular potentiometer 82 over time, as is understood by those skilled in the art. The therapist then actuates the control unit 84 and inputs the desired operating information, including angular velocity, range of motion, duration, etc. After the desired operating information is input into the control unit 84 through the keyboard 88, the therapist instructs the CPM 10 to begin operation.

Assuming the first end 34a of the first carriage member 34 is positioned at the distal end 28a of the base 28, the first carriage member 34 begins to move towards the proximal end 28a of the base 28 upon power being supplied to the motor 68. That is, as the motor 68 rotates, the screw 66 rotates therewith which thereby causes the nut 74 to move towards the proximal end 28a of the base 28. As the nut 74 moves, the first carriage member 34 moves therewith and the first and second subassemblies 102, 104 begin to expand assisted by a spring biasing means 148. As the first carriage member 34 moves across the base member 28, the microprocessor 86 monitors the relative angular velocity between the first and second carriage members 34, 40 about the first support pivot axis 54 as well as the speed of the motor 68. In accordance with the programming of the microprocessor 86, the microprocessor 86 provides pulse width modulation of the power supplied to the motor 68 to thereby control the speed of the motor 68 to achieve constant angular velocity between the first and second carriage members 34, 40 as they pivot about the first support pivot axis 54, as described above.

When the first end 34a of the first carriage member 34 reaches the proximal end 28a of the base 28, as sensed by the angular position of the first and second carriage members 34, 40, the first and second subassemblies 102, 104 are fully expanded. The microprocessor 86 then actuates the first NMES 94 to stimulate a muscle on the limb 12 depending upon how the therapist set the system prior to actuation. Once stimulation is complete, the rotational direction of the motor 68 is reversed by changing the polarity of the power such that the first end 34a of the first carriage member 34 begins to move towards the distal end 28b of the base 28 at a speed to maintain the relative angular velocity between the first and second carriage members 34, 40 constant. As the first carriage member 34 moves toward the distal end 28b of the base 28, the first and second subassemblies 102, 104 contract to a compressed state, as shown in FIG. 6, and the knee extention system 152, pivot plates 222 and limb securing means maintain the limb 12 in anatomical alignment with the first and second support pivot axis 54, 62. Once the first end 34a of the first carriage member 34 reaches the distal end 28b of the base 28, the other NMES 96 device is actuated to stimulate one of the body portions. The CPM 10 then continues in the same cycle until the desired duration of operation is complete.

From the foregoing description, it can be seen that the present invention comprises a bilateral anatomically correct continuous passive motion orthosis device for a limb. It will be appreciated by those skilled in the art that changes could be made to the embodiment described in the foregoing description without departing from the broad inventive concept thereof. It is understood, therefore, that the invention is not limited to the particular embodiment disclosed, but is intended to cover all modifications which are within the spirit and scope of the invention as defined by the appended claims.

We claim:

1. An anatomically correct continuous passive motion device for a leg, the leg being formed by an ankle, a calf, a thigh and a hip, the calf being pivotably connected to the thigh to form a knee joint such that calf is pivotable with respect to thigh about a knee joint pivot axis, the thigh being pivotably connected to hip to form a hip joint such that the thigh is pivotable with respect to the pelvic region about a hip joint pivot axis, said device comprising:

a base having a proximal end and a distal end;

a first carriage member for receiving the calf, said first carriage member having a first end and a second end;

a second carriage member for receiving the thigh, said second carriage member having a first end and a second end, said first end of said second carriage member being spaced from said second end of said second carriage member a predetermined distance;

first hinge means interconnecting between said second end of said first carriage member and said first end of said second carriage member such that said first carriage member is pivotable with respect to said second carriage member about a first support pivot axis;

drive means interconnected between said base and said first carriage member for reciprocally moving said first carriage member between the distal end of said base and proximal end of said base; and second hinge means interconnecting said second carriage member and said base such that said second carriage member is pivotable about a second virtual support pivot axis, said second support pivot axis being spaced from said second hinge means and said proximal end of said base, the calf and thigh being respectively positionable on said first and second carriage members such that the knee and hip joint pivot axes are generally aligned with said first and second support pivot axes, respectively, said second hinge means comprising an expanding assembly having a first end attached to said base adjacent to said proximal end of said base and a second end attached to the second end of said second carriage member such that the second end of said assembly moves away from said first end of said assembly along an arcuate path as said first carriage member moves from said distal end of said base toward said proximal end of said base and said second end of said assembly moves toward said first end of said assembly as said first carriage member moves from said proximal end of said base toward said distal end of said base whereby the knee and hip joint pivot axes and the first and second support pivot axes, respectively, remain aligned as said first carriage member moves between said distal and proximal ends of said base.

2. An anatomically correct continuous passive motion orthosis device for a limb, the limb being formed by a first body portion having a first end and a second end, a second body portion having a first end and a second end, and a third body portion, the first end of the first body portion being pivotably connected to the second end of the second body portion to form a first joint such that the first body portion is pivotable with respect to the second body portion about a first joint pivot axis, the first end of the second body portion being pivotably connected to the third body portion to form a second joint such that the second body portion is pivotable with respect to the third body portion about a second joint pivot axis, said device comprising:

a base having a proximal end and a distal end;

a first carriage member for receiving the first body portion of the limb, said first carriage member having a first end and a second end;

a second carriage member for receiving the second body portion of the limb, said second carriage member having a first end and a second end;

first hinge means interconnecting said second end of said first carriage member and said first end of said second carriage member such that said first carriage member is pivotable with respect to said second carriage member about a first support pivot axis;

drive means interconnected between said base and said first carriage member for reciprocally moving said first carriage member between the distal end of said base and proximal end of said base; and second hinge means interconnecting said second carriage member and said base such that said second carriage member is pivotable about a second virtual support pivot axis, said second support pivot axis being spaced from said second hinge means and said proximal end of said base, the first and second body portions being respectively positionable on said first and second carriage members such that the first and second joint pivot axes are generally aligned with said first and second support pivot axes, respectively, said second hinge means comprising an expanding assembly having a first end attached to said base adjacent to said proximal end of said base and a second end attached to the second end of said second carriage member such that said second end of said assembly moves away from said first end of said assembly as said first carriage member moves from said distal end of said base toward said proximal end of said base and said second end of said assembly moves toward said first end of said assembly as said first carriage member moves from said proximal end of said base toward said distal end of said base whereby the first and second joint pivot axes and the first and second support pivot axes, respectively, remain aligned as said first carriage member moves between said distal and proximal ends of said base.

3. The device as recited in claim 2 wherein said expanding assembly expands telescopically.

4. The device as recited in claim 2 wherein said assembly expands along an arcuate path whose radial center is aligned with the second joint of said limb.

5. The device as recited in claim 2 wherein said assembly further includes biasing means for biasing said assembly to an expanded position.

6. The device as recited in claim 5 wherein said biasing means is a spring.

* * * * *